(12) United States Patent
Hochrein et al.

(10) Patent No.: US 11,696,979 B2
(45) Date of Patent: Jul. 11, 2023

(54) DEVICE FOR CONNECTION STATUS IDENTIFICATION

(71) Applicant: FRESENIUS MEDICAL CARE DEUTSCHLAND GMBH, Bad Homburg (DE)

(72) Inventors: Torsten Hochrein, Eschenau (DE); Stefan Saal, Schonungen (DE); Frank Hedmann, Volkach (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 709 days.

(21) Appl. No.: 16/628,042

(22) PCT Filed: Jun. 28, 2018

(86) PCT No.: PCT/EP2018/067489
§ 371 (c)(1),
(2) Date: Jan. 2, 2020

(87) PCT Pub. No.: WO2019/007816
PCT Pub. Date: Jan. 10, 2019

(65) Prior Publication Data
US 2021/0138141 A1 May 13, 2021

(30) Foreign Application Priority Data
Jul. 3, 2017 (DE) .................. 10 2017 114 800.0

(51) Int. Cl.
*A61M 1/28* (2006.01)
*A61M 39/10* (2006.01)

(52) U.S. Cl.
CPC ............ *A61M 1/285* (2013.01); *A61M 39/10* (2013.01); *A61M 2039/1005* (2013.01); *A61M 2205/14* (2013.01); *A61M 2205/3317* (2013.01)

(58) Field of Classification Search
CPC ........ A61M 1/28; A61M 1/281; A61M 1/282; A61M 1/284; A61M 1/285; A61M 1/3656;
(Continued)

(56) References Cited

U.S. PATENT DOCUMENTS 5,405,336 A * 4/1995 Austin ............ A61M 25/0014
604/534
6,851,427 B1 2/2005 Nashed
(Continued)

FOREIGN PATENT DOCUMENTS

CN 201656934 U * 11/2010 ............ H03H 11/04
DE 19814047 5/1999
(Continued)

*Primary Examiner* — Kami A Bosworth
(74) *Attorney, Agent, or Firm* — Jacobson Holman PLLC

(57) ABSTRACT

The present invention relates to a device for identifying the connection status between a patient catheter and a cassette system having flexible tubing assembly, which is intended to be used in a dialysis machine, wherein the device comprises the cassette system having flexible tubing assembly and an electrical circuit, which is disposed on the cassette system having flexible tubing assembly as well as on the patient catheter, and wherein the device furthermore comprises a measuring device for measuring at least one electrical property of the electrical circuit, which depends on said connection status.

11 Claims, 1 Drawing Sheet

(58) Field of Classification Search
CPC .......... A61M 39/10; A61M 2039/1005; A61M 2205/14; A61M 2205/3317
See application file for complete search history.

(56) References Cited

U.S. PATENT DOCUMENTS

| | | | | |
|---|---|---|---|---|
| 2009/0007642 | A1* | 1/2009 | Busby | A61M 1/28 73/61.44 |
| 2009/0088683 | A1* | 4/2009 | Roger | A61M 1/3656 604/4.01 |
| 2011/0105877 | A1* | 5/2011 | Wilt | A61M 1/3655 600/381 |
| 2012/0078181 | A1* | 3/2012 | Smith | A61M 5/1452 604/404 |
| 2014/0262252 | A1 | 9/2014 | Slepicka et al. | |
| 2015/0306365 | A1* | 10/2015 | Besko | A61M 39/10 604/111 |
| 2016/0015957 | A1* | 1/2016 | Tieck | G01V 3/02 604/533 |
| 2016/0030658 | A1* | 2/2016 | van der Merwe | A61M 1/3656 604/67 |

FOREIGN PATENT DOCUMENTS

| | | | |
|---|---|---|---|
| EP | 1127583 A2 * | 8/2001 | ........ A61M 16/0816 |
| EP | 1 494 737 | 1/2005 | |
| WO | WO2008/106452 | 9/2008 | |
| WO | WO2015/162603 | 10/2015 | |
| WO | WO-2018150268 A1 * | 8/2018 | ....... A61F 13/00068 |

* cited by examiner

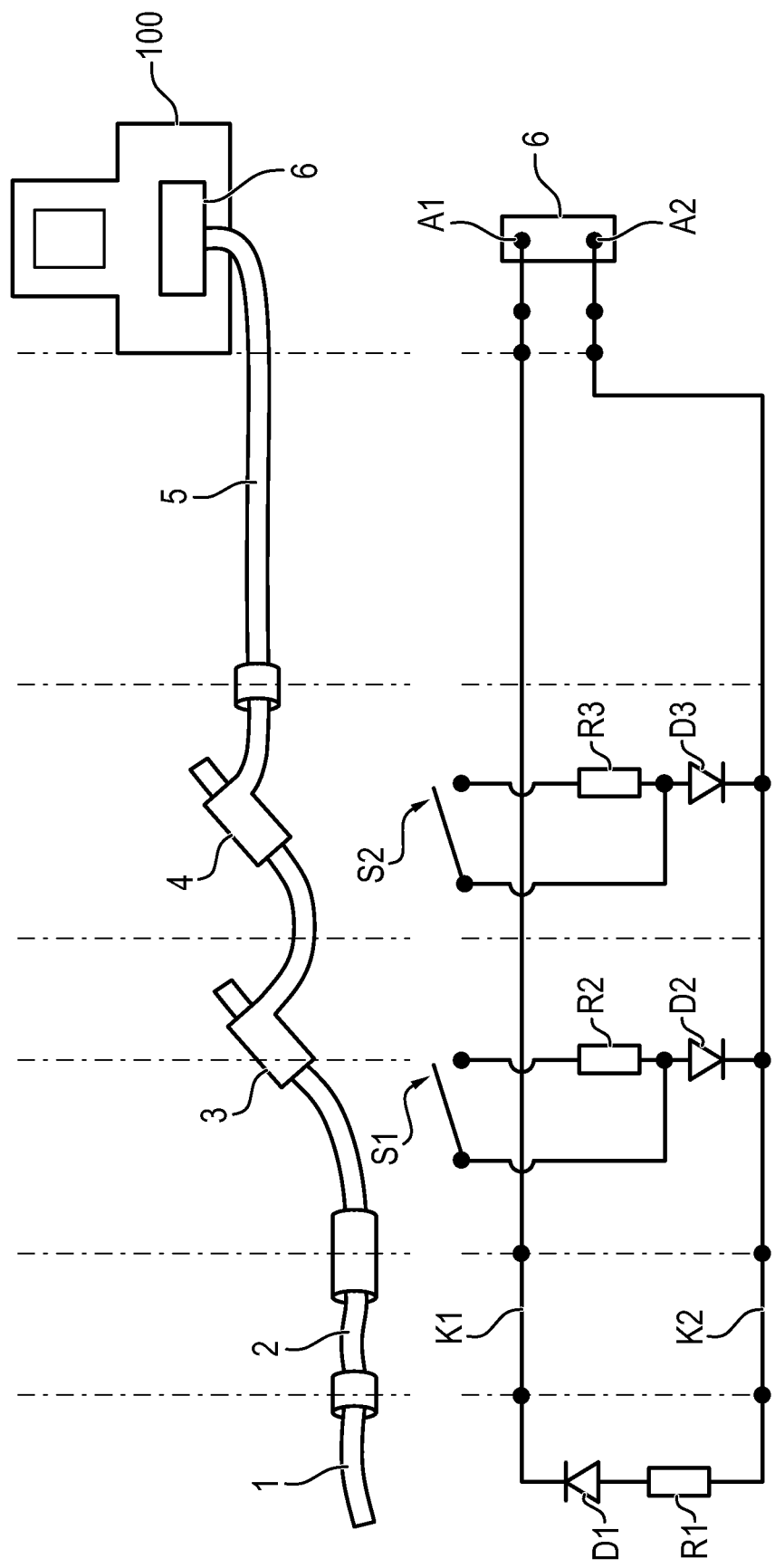

DEVICE FOR CONNECTION STATUS IDENTIFICATION

The present invention relates to a device for identifying the connection status between a patient catheter and a cassette system having flexible tubing assembly, which is intended to be used in a dialysis machine.

In peritoneal dialysis, the patient catheter implanted in the patient is connected to a disposable product, through which the dialysis solution is passed to the patient catheter, and therethrough enters into the abdominal cavity of the patient. Furthermore, the disposable product is for discharging the dialysis solution from the abdominal cavity and guiding it into a drainage bag, after a specified residence time.

The disposable product is a disposable article, which will be disposed of following treatment.

With the existing peritoneal dialysis treatments, the problem resides in that the connection status between the patient catheter and the disposable product cannot reliably be identified. Known peritoneal dialysis machines are not able to detect loosening of the mechanical connection to the patient connector, which mechanical connection commonly is formed as a swivel connection. As a consequence, the machine does not aspirate any dialysate, but possibly aspires germ-contaminated foreign air through the orifice in the disposable product.

With known peritoneal dialysis applications, the patient is required to communicate to the peritoneal dialysis machine, in the following also simply referred to as "machine", weather he is connected to the machine via the tubing system, i.e. via the disposable product. This approach is comparably inconvenient and prone to errors, as it requires interaction between the patient and the machine. Besides, checking the correct connection with the machine by the patient is difficult, as when contact to the machine or the disposable product is made, the risk of germ contamination arises. Thus, when re-adjusting the disposable product, germs may eventually invade the tubing system, which is absolutely to be avoided, as said germs eventually may result in inflammation of the peritoneum or may have other undesirable side effects.

Thus, the object of the present invention is to provide a device for identifying the connection status between the patient and the disposable product, which does not require the patient to take any action and which may automatically be performed.

This object will be solved by a device for identifying the connection status between a patient catheter and a cassette system having flexible tubing assembly, which is designed to be used in a dialysis machine, characterized in that the device comprises the cassette system having flexible tubing assembly and an electrical circuit, which is disposed on the cassette system having flexible tubing assembly as well as on the patient catheter, and in that the device furthermore comprises a measuring device for measuring at least one electrical property of the electrical circuit, which depends on said connection status. Accordingly, it is provided for the device to comprise the cassette system having flexible tubing assembly and an electrical circuit, which is disposed both on the cassette system having flexible tubing assembly and the patient catheter and the device furthermore to comprise a measuring device for measuring at least one electrical property of the electrical circuit depending on said connection status.

Thus, the present invention is based on the idea of providing the disposable product as well as a portion of the patient catheter, in the following also referred to as "catheter portion", with an electrical conductor or with a circuit, respectively, by means of which it may be verified weather the connection between the patient and the machine or the disposable product, respectively, has been carried out correctly or not. The term "patient catheter" also comprises any catheter extension.

The term "tubing system", "disposable product" and "cassette system having flexible tubing assembly" are used interchangeably in the context of the present invention, characterizing the line section between the implanted patient catheter and the peritoneal dialysis machine. This line section generally includes a cassette disposed in the machine, from which cassette the patient line extends. Typically, said line section is connected to the patient catheter via a patient connector. However, the present invention is not limited to such an arrangement, but comprises any disposable product, by means of which fresh dialysis solution may be supplied to the patient and/or spent dialysis solution may be withdrawn from the patient.

By the measuring device, which preferably is arranged in the peritoneal dialysis machine, at least one electrical parameter of the above-mentioned circuit may be measured, which may be indicative of the connection status.

Preferably, the electrical parameter is the electrical resistivity. Alternatively or in addition, other electrical variables, such as for example amperage, voltage, impedance etc. may also be taken into account.

In one conceivable configuration, the patient catheter includes a diode resistive network.

Furthermore, the cassette system having flexible tubing assembly may include a patient connector, which is provided with a diode resistive network and a switch disposed in parallel.

In the state of being ready for treatment, the patient connector is coupled with the connector of the patient catheter.

The diode of the diode resistive network of the catheter portion may be arranged antiparallel to the diode of the diode resistive network of the patient connector.

In another configuration of the invention, the cassette system having flexible tubing assembly may include a patient line, which is provided with a contact line.

Preferably, the cassette system having flexible tubing assembly includes a cassette portion, which is provided with contact points on the surface of the cassette portion. For example, by press-molding the cassette with the contacts that are incorporated in the engine block of the machine, electrical connection between the machine and the cassette, and consequently with the disposable product may be created. For this, the cassette cover foil or the cassette surface, respectively, may for example be printed or covered with a conductive color or another conductive coating.

In another preferred embodiment of the invention, it is provided for the measuring device to be formed to measure the resistivity of the diode resistive network of the catheter portion and to derive disconnection of the patient or the patient catheter, respectively, if said resistivity is infinite. It may thus be verified in a comparatively simple manner if the patient is still connected to the machine or not.

It is furthermore conceivable to measure the resistivity of the diode resistive network of the patient connector and to derive a locked patient connector, if a short circuit will be measured, due to the switch being locked in that case. Consequently, it may be detected by simple measurement if the patient connector is locked or not. If the patient connector is locked, said connector blocks the line between the cassette and the patient, so that no flow is allowed through the disposable product.

The measuring device may also be designed to detect lack of resistivity of the diode resistivity network of a patient connector, and therefrom to derive the removal of the patient connector. In this way, it may be verified if, and—in case of a plurality of patient connectors being arranged in series— which patient connector has been made use of for disconnection.

Preferably, a patient connector is a connector, as it is described in DE 198 14 047 C1. In this respect, reference will be made to the disclosure of this document. Preferably, it is provided for the switch of the diode resistivity network to be closed if the connector is locked.

In another configuration of the invention, it is provided for the measuring device to be designed for deriving the type of the cassette system having flexible tubing assembly by detecting an electrical property of the cassette system having flexible tubing assembly. In order to be able to assure clear distinction, e.g. between a cassette tubing set for regular treatment and pediatric treatment, it is thus also conceivable that by resistivity coding of the cassette or an arrangement of electrically conductive members at different positions, distinction between different types of disposables may safely be done.

Preferably, the measuring device is designed to automatedly perform the measurement. Intervention of the patient or interaction with the patient is not required in this case.

A display device may be provided, which is connected to the measuring device and is designed to output the result of the measurement detected by the measuring device, or any information based thereon. Thus, for example, from resistivity measurement, notifications such as "patient not connected to machine", "patient connector not connected", "patient connector locked" etc. may be generated.

Furthermore, the present invention relates to a dialysis machine, especially a peritoneal dialysis machine, wherein the dialysis machine is provided with the device according to the invention as described herein.

At that point it is to be noted that the terms "a" and "an" do not necessarily refer to exactly one of the members, even though this represents a possible configuration, but may also include a plurality of the members. Similarly, using the plural form also includes the presence of the member in question in the singular form, and inversely, the singular form as well includes several of the members in question.

Further details and advantages of the invention will be explained in greater detail by way of a working example represented in the drawing, wherein the only FIGURE shows a view of a disposable product as well as a portion of the patient catheter in the upper panel of the FIGURE and below the electrical circuit, with which the disposable part as well as the patient catheter is provided.

The disposable product including patient catheter is divided into six portions as follows:
reference number 1: patient catheter,
reference number 2: patient catheter extension,
reference number 3: first patient connector,
reference number 4: second patient connector,
reference number 5: patient line,
reference number 6: set or cassette in machine, respectively As it may further be seen from the FIGURE, the catheter 1, i.e. the patient catheter, which, with one portion, is implanted into the patient, is provided with a series circuit of the resistivity R1 and the diode D1, which extend between two parallel arranged contact lines K1 and K2. Said contact lines connect to the cassette 6 at the connecting points A1 and A2. The connecting points A1 and A2 conductively connect to the associated contacts of the machine 100, so that the lines K1 and K2 may be supplied with current or voltage, respectively, via the machine 100.

The disposable product, i.e. the disposable article includes the portions 3 to 6.

The catheter extension 2 extends between the patient catheter and is provided with a passage of the contact lines K1 and K2.

The patient connectors 3 and 4 are each provided with a diode resistivity network and a switch S1 and S2, as it may be seen from the FIGURE. The respective resistivities R2 and R3 are connected in series with the respective diodes D2 and D3 and extend between the contact lines K1 and K2, wherein the diodes D2 and D3 are interconnected antiparallel to the diode D1. The patient connector 3 is in contact with the patient catheter 1 or the extension 2 thereof, so that dialysis solution may flow from the disposable product to the patient catheter or vice versa from the patient catheter to the disposable product.

The patient line 5 is provided with a passage of the contact lines K1 and K2.

As set forth above, the cassette 6 comprises connecting points A1 and A2 for the contact lines K1 and K2.

Through this arrangement, the following states are detectable by a measuring device not shown in detail.
I. When Starting the Machine
   a) measure resistivity R1; patient is still connected to the machine,
   b) measure resistivity R2∥R3; both patient connectors are unlocked,
   c) measure resistivity R3; patient connector 4 is unlocked,
   d) short circuit measurement; connector is locked.
II. When Preparing the Machine
   b) measure resistivity R2∥R3; both patient connectors are unlocked,
   c) measure resistivity R3; patient connector 4 is unlocked.
From this information, the filling amount in the patient line 5 may be detected. This may be achieved by a capacitive measurement.

For example, it is conceivable that air is used as a reference, and based thereon, it may be detected by capacitive measurement, how large the filling amount of dialysis solution in the patient line is.

Due to the fact that each solution comprises a specified dielectric constant, it may furthermore be determined by the measurement of the dielectric constant if the right, i.e. the prescribed peritoneal dialysis solution, is supplied to the patient. As a result, it may be determined whether the patient is treated with the correct solution, and this eventually may be indicated to the user or the patient, respectively. Similarly, a warning message may be output and/or the treatment may be stopped or will not be started, if the non-prescribed solution is present in the patient line.
III. During Treatment
   a) measure resistivity R1; patient is still connected to the machine,
   b) resistivity R1 showing infinitely high resistivity, patient is not connected to the machine any more.
IV. Detection of Removal of the Second Patient Connector 4
   a) measure resistivity R3; R2 was removed.
V. Disconnection
   Step 1:
   a) measure short circuit; a patient connector is locked, b) measure resistivity R1; patient is still connected to the machine.

Step 2:
a) measure short circuit; a patient connector is locked,
b) resistivity R1 showing infinitely high resistivity; patient is not connected to the machine any more.

The measuring device is designed to fully-automatedly perform the above-mentioned measurements and to output the result of the measurements to a display device. On said display device, the result of the measurement or any information based thereon will subsequently be displayed to the user in an optically and/or acoustically perceptible manner.

The invention claimed is:

1. A device for identifying a connection status between a patient catheter and a cassette system having a flexible tubing assembly, the device designed to be used in a dialysis machine, wherein the device comprises the patient catheter, the cassette system having the flexible tubing assembly, an electrical circuit comprising a patient connector provided with a diode resistivity network arranged in parallel with a switch disposed on the cassette system having the flexible tubing assembly, an electrical circuit comprising a diode resistivity network disposed on the patient catheter, and a measuring device for measuring at least resistivity of the electrical circuits, the resistivity depending on said connection status, wherein the measuring device is designed to measure (i) resistivity of the diode resistivity network of the patient catheter and (ii) resistivity of the diode resistivity network of the patient connector.

2. The device according to claim 1, characterized in that a diode of the diode resistivity network of the patient catheter is disposed antiparallel to a diode of the diode resistivity network of the patient connector.

3. The device according to claim 1, characterized in that the cassette system having the flexible tubing assembly comprises a patient line provided with a contact line.

4. The device according to claim 1, characterized in that the cassette system having the flexible tubing assembly comprises a cassette portion provided with contact points on a surface of the cassette portion.

5. The device according to claim 1, characterized in that the measuring device is designed to derive disconnection of a patient if said measured resistivity of the diode resistivity network of the patient catheter is infinite.

6. The device according to claim 1, characterized in that the measuring device is further designed to derive a locked patient connector if a short circuit is measured in the resistivity of the diode resistivity network of the patient connector.

7. The device according to claim 1, characterized in that the measuring device is further designed to derive removal of the patient connector if lack of resistivity of the diode resistivity network of the patient connector is measured.

8. The device according to claim 1, characterized in that the measuring device is further designed to derive a type of the cassette system having the flexible tubing assembly by detection of an electrical property of the cassette system having the flexible tubing assembly.

9. The device according to claim 1, characterized in that the measuring device is designed to perform measurement in an automated manner.

10. The device according to claim 1, characterized in that a display device is connected to the measuring device and designed to output a result of a measurement, or any information based on the measurement, determined by the measuring device.

11. A peritoneal dialysis machine, characterized in that the peritoneal dialysis machine is provided with a device according to claim 1.

* * * * *